(12) United States Patent
Chen et al.

(10) Patent No.: US 9,651,507 B2
(45) Date of Patent: May 16, 2017

(54) HUMAN BODY BACK SCATTERING INSPECTION METHOD AND SYSTEM

(71) Applicants: Tsinghua University, Beijing (CN); Nuctech Company Limited, Beijing (CN)

(72) Inventors: Zhiqiang Chen, Beijing (CN); Ziran Zhao, Beijing (CN); Yuanjing Li, Beijing (CN); Wanlong Wu, Beijing (CN); Ming Ruan, Beijing (CN); Li Zhang, Beijing (CN); Yingkang Jin, Beijing (CN); Le Tang, Beijing (CN); Xianli Ding, Beijing (CN); Chenguang Zhu, Beijing (CN)

(73) Assignees: NUCTECH COMPANY LIMITED, Beijing (CN); TSINGHUA UNIVERSITY, Beijing (CN)

( * ) Notice: Subject to any disclaimer, the term of this patent is extended or adjusted under 35 U.S.C. 154(b) by 182 days.

(21) Appl. No.: 14/572,528

(22) Filed: Dec. 16, 2014

(65) Prior Publication Data

US 2015/0241368 A1 Aug. 27, 2015

(30) Foreign Application Priority Data

Feb. 24, 2014 (CN) .......................... 2014 1 0061813

(51) Int. Cl.
*G01N 23/203* (2006.01)
*G01T 1/167* (2006.01)
*G01V 5/00* (2006.01)

(52) U.S. Cl.
CPC ........... *G01N 23/203* (2013.01); *G01T 1/167* (2013.01); *G01V 5/0025* (2013.01); *G01V 5/0091* (2013.01)

(58) Field of Classification Search
CPC .... G01N 23/203; G01N 23/04; G01N 23/201; G01V 5/0025
See application file for complete search history.

(56) References Cited

U.S. PATENT DOCUMENTS

| 5,181,234 A | 1/1993 | Smith |
| 2009/0175412 A1 | 7/2009 | Grodzins et al. |

(Continued)

FOREIGN PATENT DOCUMENTS

| CA | 2083064 C | 2/1992 |
| CN | 202929217 U | 5/2013 |

(Continued)

OTHER PUBLICATIONS

Russian Office Action dated May 13, 2016 for Russian Application No. 2014151621.

(Continued)

*Primary Examiner* — Hoon Song
(74) *Attorney, Agent, or Firm* — Knobbe, Martens, Olson & Bear LLP

(57) ABSTRACT

A human body back-scattering inspection method and system are discloses. The method includes: obtaining a back-scattering scan image of a human body under inspection; distinguishing a body image from a background image in the back-scattering scan image; and calculating a feature parameter of the background image to determine whether radioactive substance is carried with the human body. With some embodiments of the present disclosure, it is possible to determine whether any radioactive substance is carried with a human body during back-scattering inspection of the human body. In further embodiments of the present disclosure, it is possible to approximately determine which part(s) of the human body carries the radioactive substance. This improves efficiency of inspection.

14 Claims, 3 Drawing Sheets

(56) References Cited

U.S. PATENT DOCUMENTS

2011/0274249 A1    11/2011  Gray et al.
2011/0274250 A1*   11/2011  Gray .................... G01V 5/0025
                                                              378/87
2014/0056410 A1     2/2014  Zhao et al.

FOREIGN PATENT DOCUMENTS

CN        103403534 A       11/2013
EP         2 703 849 A1      3/2014
WO        WO 01/73415 A2    10/2001

OTHER PUBLICATIONS

Extended European Search Report in corresponding European Application No. 14275262.5, dated Jul. 23, 2015.
Office Action received in Chinese Application No. 201410061813.1 dated Feb. 22, 2017.

* cited by examiner

HUMAN BODY BACK SCATTERING INSPECTION METHOD AND SYSTEM

TECHNICAL FIELD

Embodiments of the present disclosure relate to nuclear detection technology, and more particularly, to human body back-scattering inspection methods and systems for human body safety inspection and radioactive substance detection.

BACKGROUND

X-ray back-scattering imaging technology is one of mainstream technologies for safety inspection of human body. A scan image of a scattered object, i.e., human body, can be obtained by scanning the human body with X rays, receiving back-scattered signals with a large-area detector, and performing data or image processing on the signals.

Radiation source or radioactive substance is dangerous article that can be carried with a human body, in addition to dangerous contraband articles like guns, knifes, explosives and drugs. Detection of radioactive substance generally requires a detection device specifically designed for detecting radioactive substance.

Currently, X-ray back-scattering imaging devices have been widely used in critical sites like airports, and customs both domestically and abroad. These devices do not have the function of detecting radioactive substance.

SUMMARY

In view of the problem with the conventional technology, embodiments of the present disclosure provide a human body back-scattering inspection method and system which are capable of detecting radioactive substance during back-scattering inspection of human body.

According to an aspect of the disclosure, a human body back-scattering inspection method is provided, comprising: obtaining a back-scattering scan image of a human body under inspection; distinguishing a body image from a background image in the back-scattering scan image; and calculating a feature parameter of the background image to determine whether radioactive substance is carried with the human body.

In some embodiments, the step of calculating a feature parameter of the background image to determine whether radioactive substance is carried with the human body comprises: calculating an average luminance value of pixels in the background image; and determining that radioactive substance is carried with the human body if the average luminance value is larger than a preset value.

In some embodiments, the step of calculating an average luminance value of pixels in the background image comprises: integrating luminance data of the background image, and calculating an average of luminance values of the pixels as the average luminance value.

In some embodiments, it is determined that radioactive substance is carried with the human body if the average luminance value is larger than $N_{Ok}+n\times\sigma_k$, wherein $N_{Ok}$ represents a mean value of background luminance, $\sigma_k$ represents a variance of fluctuations in $N_{Ok}$ for a time period, n represents a variance multiplication coefficient, and k represents the number of pixels in the background image.

In some embodiments, the human body back-scattering inspection method further comprises: dividing the background image into a plurality of parts; calculating an average luminance value of pixels in each of the parts; and determining that the radioactive substance is hidden in a part of the body corresponding to the part of the background image having the largest average luminance value.

In some embodiments, a back-scattering detector comprising a plurality of detector modules is used to scan the human body, and the method further comprises: calculating an average luminance value for each of the detector modules; and determining the radioactive substance is hidden in a part of the body corresponding to the detector module having the largest average luminance value.

In some embodiments, the human body back-scattering inspection method further comprises: dividing the background image into a plurality of parts; calculating an average luminance value of pixels in each of the parts; and determining that the radioactive substance is hidden in parts of the body corresponding to the parts of the background image each having an average luminance value larger than the preset value.

In some embodiments, a back-scattering detector comprising a plurality of detector modules is used to scan the human body, and the method further comprises: calculating an average luminance value for each of the detector modules; and determining the radioactive substance is hidden in parts of the body corresponding to the detector modules each having the average luminance value larger than the preset value.

According to another aspect of the disclosure, a human body back-scattering inspection system is provided, comprising: a ray generator configured to generate a ray beam; a flying-spot forming device configured to modulate the ray beam and form a flying-spot ray beam; a back-scattering detector configured to receive a scattered ray generated by irradiating the flying-spot ray beam onto the human body, and generate an electric signal; and a control and data processing terminal configured to obtain a back-scattering scan image of the human body based on the electric signal, distinguish a body image from a background image in the back-scattering scan image, and calculate a feature parameter of the background image to determine whether radioactive substance is carried with the human body.

In some embodiments, the control and data processing terminal calculates an average luminance value of pixels in the background image, and determines that radioactive substance is carried with the human body if the average luminance value is larger than a preset value.

In some embodiments, the control and data processing terminal integrates luminance data of the background image, and calculate an average of luminance values of the pixels as the average luminance value.

In some embodiments, the control and data processing terminal determines that radioactive substance is carried with the human body if the average luminance value is larger than $N_{Ok}+n\times\sigma_k$, wherein $N_{Ok}$ represents a mean value of background luminance, $\sigma_k$ represents a variance of fluctuations in $N_{Ok}$ for a time period, n represents a variance multiplication coefficient, and k represents the number of pixels in the background image.

In some embodiments, the control and data processing terminal divides the background image into a plurality of parts, calculates an average luminance value of pixels in each of the parts, and determines that the radioactive substance is hidden in a part of the body corresponding to the part of the background image having the largest average luminance value.

In some embodiments, the back-scattering detector comprises a plurality of detector modules, and the control and data processing terminal calculates an average luminance value for each of the detector modules, and determines the radioactive substance is hidden in a part of the body corresponding to the detector module having the largest average luminance value.

In some embodiments, the control and data processing terminal divides the background image into a plurality of parts, calculates an average luminance value of pixels in each of the parts, and determines that the radioactive substance is hidden in parts of the body corresponding to the parts of the background image each having an average luminance value larger than the preset value.

In some embodiments, the back-scattering detector comprises a plurality of detector modules, and the control and data processing terminal calculates an average luminance value for each of the detector modules, and determines the radioactive substance is hidden in parts of the body corresponding to the detector modules each having the average luminance value larger than the preset value.

According to some embodiments of the present disclosure, it is possible to determine whether any radioactive substance is carried with a human body during back-scattering inspection of the human body. According to further embodiments of the present disclosure, it is possible to approximately determine which part(s) of the human body carries the radioactive substance. This improves efficiency of inspection.

DETAILED DESCRIPTION OF THE EMBODIMENTS

The particular embodiments of the disclosure are described below in details. It shall be noted that the embodiments herein are used for illustration only, but not limiting the disclosure. In the description below, a number of particular details are explained to provide a better understanding to the disclosure. However, it is apparent to those skilled in the art the disclosure can be implemented without these particular details. In other examples, well-known circuits, materials or methods are not described so as not to obscure the disclosure.

Throughout the specification, reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that figures here are for the purpose of illustration, and not necessarily drawn to scale. It should be appreciated that "connecting" or "coupling" a component to another component may mean that the component is directly connected or coupled to the other component, or there may be a component intervening between them. On the contrary, "directly connecting" or "directly coupling" a component to another component mans that there is no intervening component. Like reference signs refer to similar elements throughout the figures. The term "and/or" used herein means any and all combinations of one or more listed items.

In view of the problem with the conventional technology, some embodiments of the present disclosure propose determining whether a human body under inspection carries any radioactive substance by using a background image from a back-scattering image of the human body. In some embodiments, for example, a back-scattering scan image of a human body under inspection is obtained in a back-scattering inspection system. Then, a body image is distinguished from a background image in the back-scattering scan image, and a feature parameter of the background image is calculated to determine whether the human body carries any radioactive substance. According to these embodiments, the background luminance of the image obtained by the back-scattering inspection system will change if the human body carries radioactive substance. Thus, it is possible to determine whether the human body carries radioactive substance based on detection of such change in background luminance.

Figure 1:
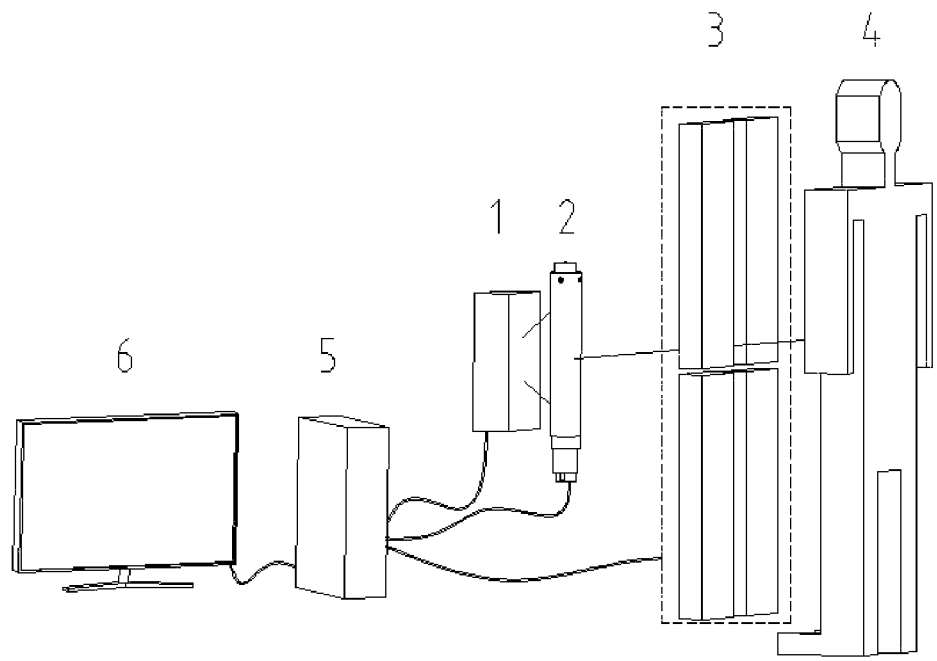
FIG. 1 illustrates a schematic block diagram of a human body back-scattering system according to an embodiment of the disclosure.

FIG. 1 illustrates a schematic block diagram of a human body back-scattering system according to an embodiment of the disclosure. As shown in FIG. 1, the human body back-scattering system includes a ray generator 1, a flying-spot forming device 2, a detector 3, a control and data processing terminal 5, and a display terminal 6. A ray beam emitted from the ray generator 1 is formed into a flying-spot ray beam through modulation of the flying-spot forming device 2, and irradiated onto a human body 4 under inspection. The detector 3 receives rays back-scatted from the human body 4, produces electric signals and provides them to the data processing terminal 5. A scan image after the processing is displayed on the terminal 6.

In some embodiments, the flying-spot forming device 2 may be in a form of rotating wheel or rotating table. The detector 3 may be arranged in another manner. For example, the detector 3 may be movable horizontally or vertically, or may be stationary.

The detector 3 of large area and high sensitivity is commonly used in the human body back-scattering system to collect, as much as possible, ray signals scattered back from the human body 4. When rays scan substance having a small atomic number, such as human body, explosives or drugs, the back-scatted rays are strong, the detector 3 receives strong signals, and the resultant image is bright. When rays scan substance having a high atomic number, such as guns or knifes, or air, the back-scatted rays are weak, the detector 3 receives weak signals, and the resultant image is dark.

Figure 2:
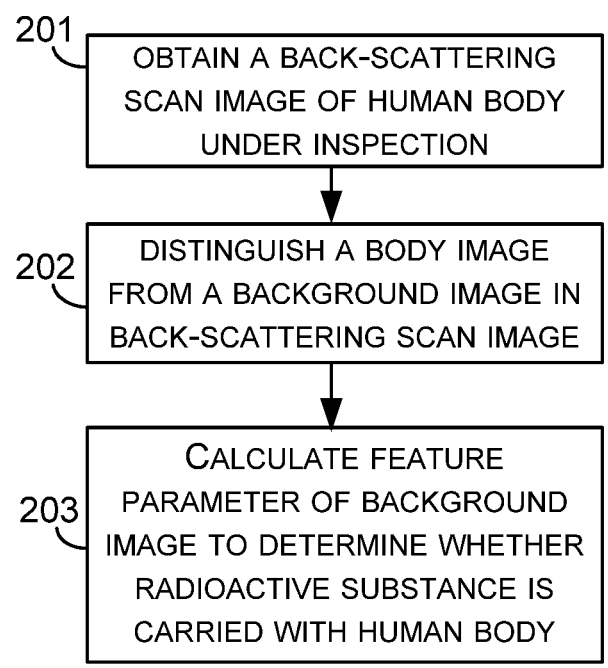
FIG. 2 illustrates a flowchart of a human body back-scattering method according to an embodiment of the disclosure.

FIG. 2 illustrates a flowchart of a human body back-scattering method according to an embodiment of the disclosure. As shown in FIG. 2, a back-scattering scan image of a human body under inspection is obtained at step 201. The back-scattering image of the human body 4 may be obtained, for example, through scanning by the human body back-scattering inspection system of FIG. 1.

Figures 3, 4:
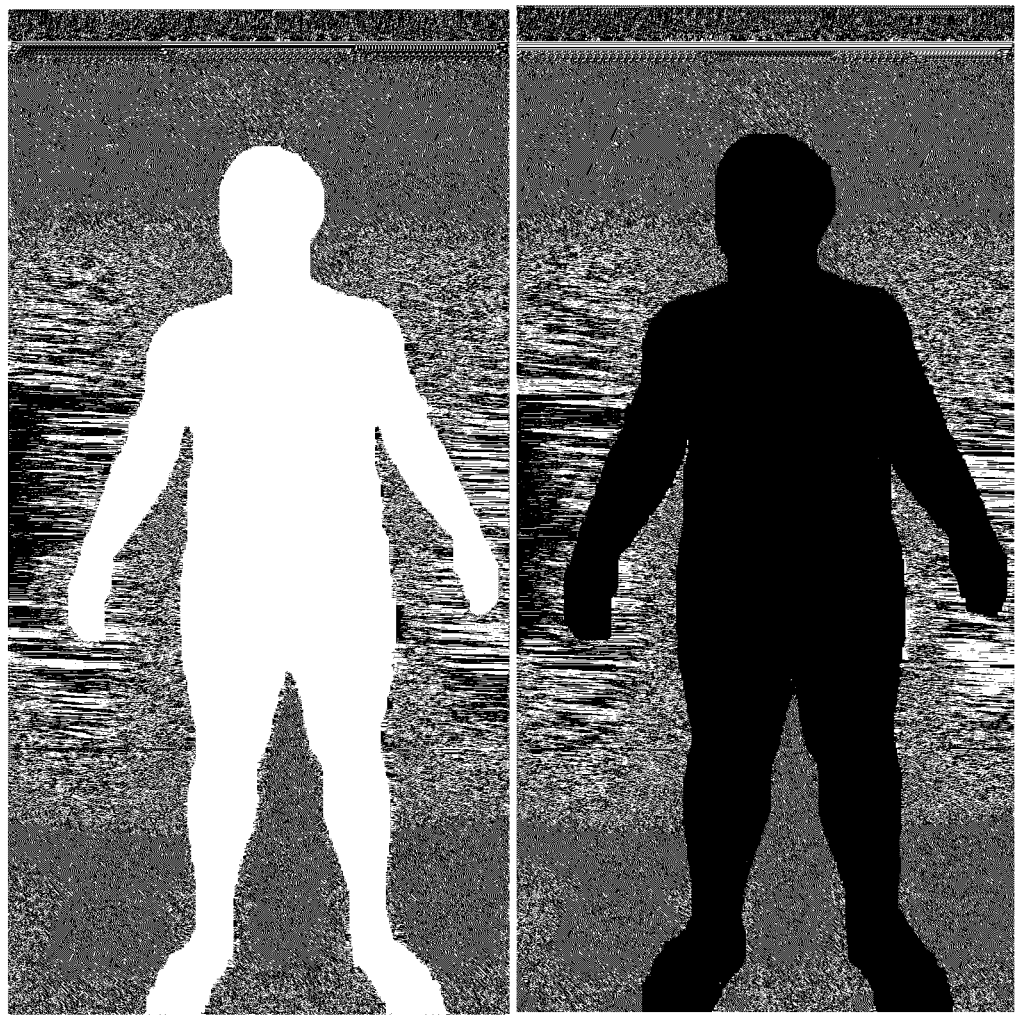
FIG. 3 illustrates a scanned body image obtained by a human body back-scattering inspection system according to an embodiment of the disclosure.
FIG. 4 illustrates a body image obtained by processing the body image of FIG. 3 according to an embodiment of the disclosure.

At step 202, a body image is distinguished from a background image in the back-scattering scan image. What is inspected by the human body back-scattering inspection system is simply a human body which has characteristics, such as a simple and distinct structure, and a continuous edge, and which is significantly different from background like air. Accordingly, in some embodiments, the body image can be separated from the background image through image recognition technology, such as binarization, and the body image data can be deducted from the entire scan image data. In further embodiments, in order to prevent clothes and the like from affecting subsequent data, the outer edge of the body image may be properly expanded to reduce influence on the radioactive substance detection from the clothes image (which is probably invisible). As shown in FIG. 4, the body image is broader and bigger than the body image of FIG. 3.

At step 203, a feature parameter of the background image is calculated to determine whether the human body carries any radioactive substance. In some embodiments, luminance data of the background image obtained by deducting the body image are integrated, and an average $N_k$ (k denotes the number of pixels) of luminance values of pixels in the background image is calculated as an average luminance value of pixels. An X-ray machine may emit ray beams to scan in the same condition no matter whether there is any human body under inspection (however, it should be guaranteed that no person carries any radioactive substance, and no external ray source around the machine). The obtained scan image may be processed in the same condition (i.e., after deduction of body image), including extracting, integrating and averaging luminance data of the background image, to obtain an average value $N_{Ok}$ (k denotes the number of pixels in the background image, and no data of human image is involved). The values $N_{Ok}$ may be measured in advance and stored in device. $N_{Ok}$ may be a series of constants, or a function of k. $N_{Ok}$ may be updated during detection, such as moving update or regular update. In a short period of time, doses for the X-ray machine and environment base are substantially stable, and $N_{Ok}$ may fluctuate with a statistic error without external ray source. In some embodiments, $N_k$ may be compared with $N_{Ok}$, and it may be determined that the human body might carries radioactive substance when $N_k$ is larger than $N_{Ok}+n\times\sigma_k$. Here, $\sigma_k$ represents a variance of fluctuations in $N_{Ok}$ for a time period, and n represents a variance multiplication coefficient. They can be adjusted according to requirements of false alarm rate.

Further, the value $\sigma_k$ is associated with $N_{Ok}$ and the number of pixels, k, for $N_{Ok}$. The value $\sigma_k$ may be determined by derivation based on mathematics statistics principle, and data statistics with a large number of experiments and tests of $N_{Ok}$. In another embodiment, the relationship among $N_{Ok}$, $\sigma_k$, and k may be stored in system, and may be updated regularly or at any time upon change in environment base dose or device condition, such as replacement of X-ray machine.

In further embodiments, it is possible to approximately determine which parts of the human body (locations) might carry the detected radioactive substance, after determining that the human body carries radioactive substance. In an example, the background image may be divided into a plurality of parts, for example, along a vertical direction or according to the closest body part. Then, an average luminance value of pixels is calculated for each of the divided parts. It may be determined that the radioactive substance is hidden in a part of the human body corresponding to the part of background image having the largest average luminance value, for example, a part of the human body that is closest to the part of background image having the largest average luminance value. In other embodiments, the average luminance value calculated for each of the divided parts may be compared with a preset value, and it may be determine that the radioactive substance is carried in parts of the human body corresponding to the divided parts having an average luminance value larger than the preset value.

Figure 5:
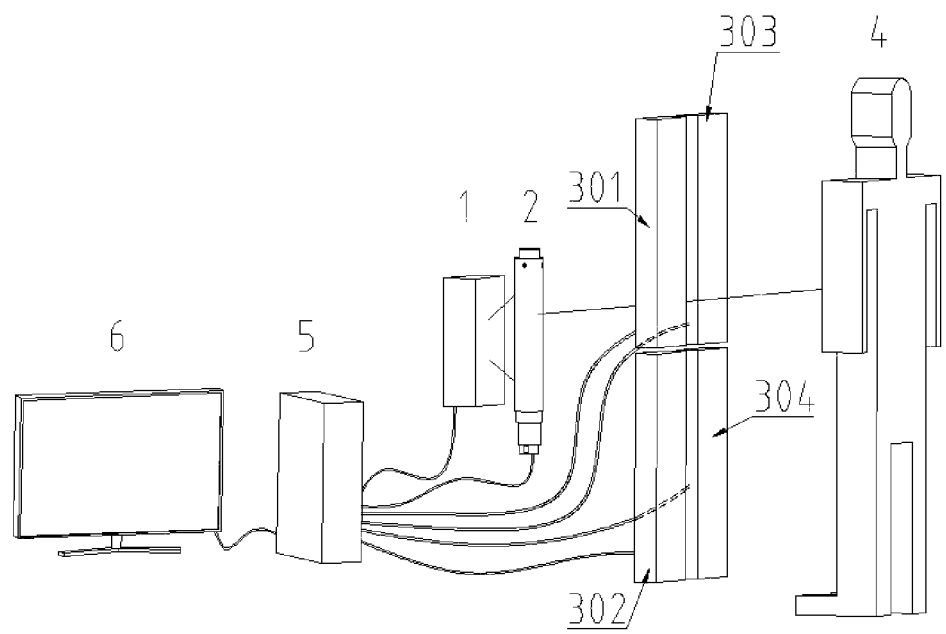
FIG. 5 illustrates a schematic block diagram of a human body back-scattering system according to another embodiment of the disclosure.

In further embodiments, the detector 3 is generally not a single detector but a combination of several detector modules, especially in human body back-scattering inspection devices in practical application. As shown in FIG. 5, the data processing terminal 5 may extract a feature parameter, such as a difference in pixel average values, from data for different detector modules 301, 302, 303, and 304, scan timings, and the like. After analysis with certain algorithm (such as center of gravity algorithm), the data processing terminal 5 may determine whether different parts of the human body carry radioactive substance, or a probability of each part carrying radioactive substance. In other embodiments, an average luminance value of pixel calculated for each of the detector module may be compared with a preset value, and it may be determine that the radioactive substance is carried in parts of the human body corresponding to the detector modules having an average luminance value larger than the preset value.

With the above embodiments, it is possible to effectively extend application scope of the human body back-scattering inspection device, increase detection of radioactive substance carried with human body, and improve inspection effects, without increasing hardware, reducing scanning speed, or affecting image quality.

While the present disclosure has been described with reference to several typical embodiments, it is apparent to those skilled in the art that the terms are used for illustration and explanation purpose and not for limitation. The present disclosure may be practiced in various forms without departing from the esprit or essence of the disclosure. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present disclosure which is defined by the claims as attached.

What is claimed is:

1. A human body back-scattering inspection method comprising:
   obtaining a back-scattering scan image of a human body under inspection;
   distinguishing a body image from a background image in the back-scattering scan image; and
   calculating a feature parameter of the background image to determine whether a radioactive substance is carried with the human body;
   wherein the calculating of the feature parameter of the background image to determine whether the radioactive substance is carried with the human body comprises:
   calculating an average luminance value of pixels in the background image; and
   determining that the radioactive substance is carried with the human body if the average luminance value is larger than a preset value.

2. The human body back-scattering inspection method according to claim 1, wherein the step of calculating an average luminance value of pixels in the background image comprises:
  integrating luminance data of the background image, and calculating an average of luminance values of the pixels as the average luminance value.

3. The human body back-scattering inspection method according to claim 2, wherein it is determined that radioactive substance is carried with the human body if the average luminance value is larger than $N_{Ok}+n \times \sigma_k$, wherein $N_{Ok}$ represents a mean value of background luminance, $\sigma_k$ represents a variance of fluctuations in $N_{Ok}$ for a time period, n represents a variance multiplication coefficient, and k represents the number of pixels in the background image.

4. The human body back-scattering inspection method according to claim 1, further comprising:
  dividing the background image into a plurality of parts;
  calculating an average luminance value of pixels in each of the parts; and
  determining that the radioactive substance is hidden in a part of the body corresponding to the part of the background image having the largest average luminance value.

5. The human body back-scattering inspection method according to claim 1, wherein a back-scattering detector comprising a plurality of detector modules is used to scan the human body, and the method further comprises:
  calculating an average luminance value for each of the detector modules; and
  determining the radioactive substance is hidden in a part of the body corresponding to the detector module having the largest average luminance value.

6. The human body back-scattering inspection method according to claim 1, further comprising:
  dividing the background image into a plurality of parts;
  calculating an average luminance value of pixels in each of the parts; and
  determining that the radioactive substance is hidden in parts of the body corresponding to the parts of the background image each having an average luminance value larger than the preset value.

7. The human body back-scattering inspection method according to claim 1, wherein a back-scattering detector comprising a plurality of detector modules is used to scan the human body, and the method further comprises:
  calculating an average luminance value for each of the detector modules; and
  determining the radioactive substance is hidden in parts of the body corresponding to the detector modules each having the average luminance value larger than the preset value.

8. A human body back-scattering inspection system comprising:
  a ray generator configured to generate a ray beam;
  a flying-spot forming device configured to modulate the ray beam and form a flying-spot ray beam;
  a back-scattering detector configured to receive a scattered ray generated by irradiating the flying-spot ray beam onto the human body, and generate an electric signal; and
  a control and data processing terminal configured to obtain a back-scattering scan image of the human body based on the electric signal, distinguish a body image from a background image in the back-scattering scan image, and calculate a feature parameter of the background image to determine whether radioactive substance is carried with the human body;
  wherein the control and data processing terminal calculates an average luminance value of pixels in the background image, and determines that the radioactive substance is carried with the human body if the average luminance value is larger than a preset value.

9. The human body back-scattering inspection system according to claim 8, wherein the control and data processing terminal integrates luminance data of the background image, and calculate an average of luminance values of the pixels as the average luminance value.

10. The human body back-scattering inspection system according to claim 9, wherein the control and data processing terminal determines that radioactive substance is carried with the human body if the average luminance value is larger than $N_{Ok}+n \times \sigma_k$, wherein $N_{Ok}$ represents a mean value of background luminance, $\sigma_k$ represents a variance of fluctuations in $N_{Ok}$ for a time period, n represents a variance multiplication coefficient, and k represents the number of pixels in the background image.

11. The human body back-scattering inspection system according to claim 8, wherein the control and data processing terminal divides the background image into a plurality of parts, calculates an average luminance value of pixels in each of the parts, and determines that the radioactive substance is hidden in a part of the body corresponding to the part of the background image having the largest average luminance value.

12. The human body back-scattering inspection system according to claim 8, wherein the back-scattering detector comprises a plurality of detector modules, and
  the control and data processing terminal calculates an average luminance value for each of the detector modules, and determines the radioactive substance is hidden in a part of the body corresponding to the detector module having the largest average luminance value.

13. The human body back-scattering inspection system according to claim 8, wherein the control and data processing terminal divides the background image into a plurality of parts, calculates an average luminance value of pixels in each of the parts, and determines that the radioactive substance is hidden in parts of the body corresponding to the parts of the background image each having an average luminance value larger than the preset value.

14. The human body back-scattering inspection system according to claim 8, wherein the back-scattering detector comprises a plurality of detector modules, and
  the control and data processing terminal calculates an average luminance value for each of the detector modules, and determines the radioactive substance is hidden in parts of the body corresponding to the detector modules each having the average luminance value larger than the preset value.

* * * * *